United States Patent
Ha et al.

(10) Patent No.: US 7,608,734 B2
(45) Date of Patent: Oct. 27, 2009

(54) METHOD OF PRODUCING UNSATURATED ACID IN FIXED-BED CATALYTIC PARTIAL OXIDATION REACTOR WITH HIGH EFFICIENCY

(75) Inventors: Kyoung Su Ha, Daejeon (KR); Boo Gon Woo, Daejeon (KR); Jun Seok Ko, Daejeon (KR); Seong Pil Kang, Daejeon (KR); Seok Hwan Choi, Daejeon (KR); Young Bae Kim, Yeosu-si (KR)

(73) Assignee: LG Chem, Ltd. (KR)

( * ) Notice: Subject to any disclaimer, the term of this patent is extended or adjusted under 35 U.S.C. 154(b) by 365 days.

(21) Appl. No.: 11/483,752

(22) Filed: Jul. 10, 2006

(65) Prior Publication Data

US 2007/0073084 A1    Mar. 29, 2007

(30) Foreign Application Priority Data

Jul. 8, 2005    (KR) .............. 10-2005-0061797

(51) Int. Cl.
    C07C 51/235    (2006.01)
    C07C 45/00     (2006.01)

(52) U.S. Cl. .............. 562/532; 562/542; 568/476

(58) Field of Classification Search .............. None
    See application file for complete search history.

(56) References Cited

U.S. PATENT DOCUMENTS

| | | | |
|---|---|---|---|
| 3,801,634 A | 4/1974 | Krabetz et al. | |
| 4,365,087 A | 12/1982 | Kadowaki et al. | |
| 4,837,360 A | 6/1989 | Kadowaki et al. | |
| 6,541,664 B1 | 4/2003 | Jachow et al. | |
| 6,613,940 B1 | 9/2003 | Nishimura et al. | |
| 7,238,836 B2* | 7/2007 | Ha et al. ............ | 562/545 |
| 2005/0049435 A1 | 3/2005 | Ha et al. | |

FOREIGN PATENT DOCUMENTS

| | | | |
|---|---|---|---|
| JP | 54021966 | | 2/1979 |
| KR | 100204728 | | 3/1999 |
| KR | 100204729 | | 3/1999 |
| KR | 100349602 | | 8/2002 |
| KR | 1020050024206 | * | 3/2005 |
| KR | 1020050024306 | | 3/2005 |
| KR | 1020050065425 | * | 6/2005 |
| WO | 2005/061414 | | 7/2005 |
| WO | 2005/063674 | | 7/2005 |
| WO | 2005061414 | * | 7/2005 |
| WO | 2005063674 | * | 7/2005 |
| WO | 2006/091005 | | 8/2006 |

OTHER PUBLICATIONS

International Search Report dated Oct. 13, 2006 for Application No. PCT/KR2006/002651 (All references cited in Search Report are listed above).

(Continued)

*Primary Examiner*—Karl J Puttlitz
(74) *Attorney, Agent, or Firm*—Cantor Colburn LLP

(57) ABSTRACT

Disclosed is a process for producing unsaturated aldehydes and/or unsaturated acids from olefins or alkanes in a fixed bed shell-and-tube heat exchanger-type reactor by catalytic vapor phase oxidation. A heat exchanger-type reactor for use in such a process is also disclosed. The process utilizes at least one first-step reaction zone and a second-step reaction zone that is divided into two or more shell spaces by at least one partition. The process may be applied to a single-step process for producing unsaturated acids from alkanes or alkenes.

16 Claims, 2 Drawing Sheets

OTHER PUBLICATIONS

Korean Office Action dated May 15, 2007 for Application No. 10-2006-0063448 (All references cited in Office Action are listed above).
Supplementary European Search Report; Application No. EP 06 78 3285 issued in corresponding European Patent Application No. 07 021 023.2 on Jan. 20, 2009 (claiming priority from Korean Patent Application No. 10-2005-0061797).
Notice of Allowance issued on Oct. 29, 2008, corresponding to Korean Patent Application No. 10-2006-0063448 (claiming priority from Korean Patent Application No. 10-2005-0061797).

* cited by examiner

METHOD OF PRODUCING UNSATURATED ACID IN FIXED-BED CATALYTIC PARTIAL OXIDATION REACTOR WITH HIGH EFFICIENCY

This application claims the benefit of the filing date of Korean Patent Application No. 2005-61797, filed on Jul. 8, 2005, in the Korean Intellectual Property Office, the disclosure of which is incorporated herein in its entirety by reference.

TECHNICAL FIELD

The present invention relates to a process for producing unsaturated aldehydes and/or unsaturated acids from olefins or alkanes in a fixed bed shell-and-tube heat exchanger-type reactor by catalytic vapor phase oxidation, as well as a heat exchanger-type reactor for use in the same process.

BACKGROUND ART

A process for producing unsaturated aldehydes and/or unsaturated acids from olefins or alkanes in vapor phase by using a catalyst is a typical process of catalytic vapor phase oxidation.

Particular examples of such catalytic vapor phase oxidation include a process for producing acrolein and/or acrylic acid by the oxidation of propylene or propane, or a process for producing methacrolein and/or methacrylic acid by the oxidation of isobutylene, isobutane, t-butyl alcohol or methyl t-butyl ether.

Generally, catalytic vapor phase oxidation is carried out by charging one or more kinds of granular catalysts into a reaction tube (catalytic tube), supplying feed gas into a reactor through a pipe, and contacting the feed gas with the catalyst in the reaction tube. Reaction heat generated during the reaction is removed by heat exchange with a heat transfer medium whose temperature is maintained at a predetermined temperature. The heat transfer medium for heat exchange is provided on the outer surface of the reaction tube so as to perform heat transfer. The reaction mixture containing a desired product is collected and recovered through a pipe, and sent to a purification step. Since the catalytic vapor phase oxidation is a highly exothermic reaction, it is very important to maintain reaction temperature within a certain range and to reduce the magnitude of a hot spot occurring in a reaction zone. It is also very important to disperse heat at a site where heat accumulation may occur due to the structure of a reactor or a catalyst layer.

The partial oxidation of olefins or alkanes corresponding thereto uses a multimetal oxide containing molybdenum and bismuth or vanadium or a mixture thereof, as a catalyst.

Generally, (meth)acrylic acid, a final product, is produced from propylene, propane, isobutylene, isobutane, t-butyl alcohol or methyl-t-butyl ether (referred to as 'propylene or the like', hereinafter) by a two-step process of vapor phase catalytic partial oxidation. More particularly, in the first step, propylene or the like is oxidized by oxygen, inert gas for dilution, water steam and a certain amount of a catalyst, so as to produce (meth)acrolein as a main product. Then, in the second step, the (meth)acrolein is oxidized by oxygen, inert gas for dilution, water steam and a certain amount of a catalyst, so as to produce (meth)acrylic acid. The catalyst used in the first step is a Mo-Bi-based oxidation catalyst, which oxidizes propylene or the like to produce (meth)acrolein as a main product. Also, some acrolein is continuously oxidized on the same catalyst to partially produce (meth)acrylic acid. The catalyst used in the second step is a Mo-V-based oxidation catalyst, which mainly oxidizes (meth)acrolein in the mixed gas containing the (meth)acrolein produced from the first step to produce (meth)acrylic acid as a main product.

A reactor for performing the aforementioned process is provided either in such a manner that both the two-steps can be performed in one system, or in such a manner that the two steps can be performed in different systems.

Recently, a catalyst for use in producing unsaturated acids such as (meth)acrylic acid from alkanes such as propane or isobutane via a single-step process has been developed.

Meanwhile, (meth)acrylic acid manufacturers now conduct diversified efforts either to improve the structure of the reactor so as to increase the production of acrylic acid by the reactor, or to propose the most suitable catalyst to induce oxidation, or to improve process operations.

In part of such prior efforts, propylene or the like which is supplied into the reactor is used at high space velocity and high concentration. However, in this case, rapid oxidation occurs in the reactor, which makes it difficult to control the resultant reaction temperature. Also, a hot spot is generated in the catalyst layer of the reactor, and heat accumulation occurs in the vicinity of the hot spot, resulting in increased production of byproducts, such as carbon monoxide, carbon dioxide and acetic acid at high temperature, and in a drop in yield of (meth)acrylic acid.

Furthermore, production of (meth)acrylic acid using high space velocity and high concentration of propylene or the like causes various problems, as the reaction temperature abnormally increases in the reactor, such problems including the loss of active ingredients from the catalyst layer, a drop in the number of active sites caused by sintering of metal components, or the like. Consequently, this leads to deterioration of the function of the catalyst layer.

Accordingly, in the production of (meth)acrylic acid, control of the reaction heat in the relevant reactor is of great importance. Particularly, not only the formation of hot spots in the catalyst layer but also the accumulation of heat in the vicinity of the hot spots must be inhibited, and the reactor must be effectively controlled so that the hot spots do not lead to reactor runaway (a state where the reactor cannot be controlled or explodes by a highly exothermic reaction). Therefore, it is very important to inhibit hot spots and heat accumulation in the vicinity of the hot spots so as to extend the lifetime of the catalyst, to inhibit side reactions, and thus to increase yield of (meth)acrylic acid.

DISCLOSURE OF THE INVENTION

The inventors of the present invention have made improvements in a fixed-bed shell-and-tube heat exchanger-type reactor for producing unsaturated aldehydes and/or unsaturated acids from olefins. In the improvements, at least one reaction zone of the first-step reaction zone and the second-step reaction zone was divided into two or more shell spaces along the axial direction by at least one partition, and the temperature of a heat transfer medium filled in each of the divided shell spaces was set to a temperature suitable for the activity of a catalyst and the degree of reaction. As a result of such improvements, the present inventors have found that a hot spot and heat accumulation in the vicinity of the hot spot could be inhibited. The present invention is based on this finding.

Additionally, the present invention may be applied to a single-step process for producing unsaturated acids from alkanes, for example, a process for producing (meth)acrylic acid from propane or isobutane.

In one aspect, the present invention provides a process for producing unsaturated aldehydes from olefins, particularly a process for producing (meth)acrolein from propylene or the like, by fixed-bed catalytic partial oxidation in a shell-and-tube heat exchanger-type reactor, wherein the reactor comprises a reaction zone for producing the unsaturated aldehydes; the reaction zone is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to [the lowest active temperature+20° C.], when referring to the two or more shell spaces sequentially as the first shell space, the second shell space, . . . , the $n^{th}$ shell space; and the first shell space is controlled in such a manner that it provides an olefin conversion contribution per length as defined in the following equation of 1.2~2.5:

[Equation 1]

Olefin conversion contribution per length=(mole number of olefins that have reacted in the relevant catalyst layer zone/mole number of the total olefins supplied to the reaction zone)/volumetric ratio of the relevant catalyst layer zone to the total catalyst layer of the reaction zone.

In another aspect, the present invention provides a process for producing unsaturated acids from unsaturated aldehydes or alkanes, particularly a process for producing (meth)acrylic acid from (meth)acrolein, propane or isobutane, by fixed-bed catalytic partial oxidation in a shell-and-tube heat exchanger-type reactor, wherein the reactor comprises a reaction zone for producing the unsaturated acids; the reaction zone is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to [the lowest active temperature+20° C.], when referring to the two or more shell spaces sequentially as the first shell space, the second shell space, . . . , the $n^{th}$ shell space; and the first shell space is controlled in such a manner that it provides an unsaturated aldehyde or alkane conversion contribution per length as defined in the following equation of 1.2~2.5:

[Equation 2]

Unsaturated aldehyde or alkane conversion contribution per length=(mole number of unsaturated aldehydes or alkanes that have reacted in the relevant catalyst layer zone/ mole number of the total unsaturated aldehydes or alkanes supplied to the reaction zone)/volumetric ratio of the relevant catalyst layer zone to the total catalyst layer of the reaction zone.

In still another aspect, the present invention provides a shell-and-tube heat exchanger-type reactor which can be used in a process for producing unsaturated aldehydes and unsaturated acids from olefins by fixed-bed catalytic partial oxidation, the reactor comprising one or more catalytic tubes each including a first-step reaction zone for mainly producing the unsaturated aldehydes, and a second-step reaction zone for mainly producing the unsaturated acids, or both the two zones, wherein at least one of the first-step reaction zone and the second-step reaction zone is divided into two or more shell spaces by at least one partition; each of the divided shell spaces is independently heat-controlled; a heat transfer medium in the first shell space of the first-step reaction zone or the first shell space of the second-step reaction zone has a temperature ranging from the lowest active temperature of a catalyst layer packed in a reaction tube corresponding to the first shell space of the first-step reaction zone or the first shell space of the second-step reaction zone to [the lowest active temperature+20° C.], when referring to the two or more shell spaces corresponding to the first-step reaction zone sequentially as the first shell space of the first-step reaction zone, the second shell space of the first-step reaction zone, . . . , the $n^{th}$ shell space of the first-step reaction zone, and the two or more shell spaces corresponding to the second-step reaction zone sequentially as the first shell space of the second-step reaction zone, the second shell space of the second-step reaction zone, . . . , the $n^{th}$ shell space of the second-step reaction zone; and the first shell space of the first-step reaction zone or the first shell space of the second-step reaction zone is controlled in such a manner that it provides a reactant conversion contribution per length as defined in Equation 1 or 2 of 1.2~2.5.

In yet another aspect, the present invention provides a shell-and-tube heat exchanger-type reactor which can be used in a process for producing unsaturated acids from alkanes by fixed-bed catalytic partial oxidation, the reactor comprising one or more catalytic tubes each including a reaction zone for producing the unsaturated acids, wherein the reaction zone is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to [the lowest active temperature+20° C.], when referring to the two or more shell spaces sequentially as the first shell space, the second shell space, . . . , the $n^{th}$ shell space; and the first shell space is controlled in such a manner that it provides an alkane conversion contribution per length as defined in Equation 2 of 1.2~2.5.

Hereinafter, the present invention will be explained in more detail.

(1) Disposition of Partition

The inventors of the present invention have conducted many studies and obtained the following results. When a catalyst having a high activity corresponding to a conversion of 96% or more in the first-step reaction zone (for example, a catalyst having a conversion of 96% at a temperature, where the highest catalytic activity can be obtained, under a space velocity of feed of 1500 $hr^{-1}$ and that of an olefin of 100 $hr^{-1}$) is packed in the first-step reaction zone and the reaction zone is operated with no temperature control along the axial direction, a hot spot having a temperature near the sintering temperature of the catalyst is generated in the front portion of the first-step reaction zone. Additionally, when a catalyst having a high activity corresponding to an acrolein conversion of 95% or more in the second-step reaction zone (for example, a catalyst having a conversion of 95% at a temperature, where the highest catalytic activity can be obtained, under a space velocity of unsaturated aldehydes of 90 $hr^{-1}$) is packed in the second-step reaction zone and the reaction zone is operated with no independent temperature control along the axial direction, a hot spot having a temperature near the sintering temperature of the catalyst is generated in the front portion of the second-step reaction zone. Such problem of hot spots also occurs in a single-step process for producing unsaturated acids from alkanes.

In addition, it is not possible to sufficiently control the reaction heat of catalytic vapor phase oxidation mere by circulating a heat transfer medium uniformly in a reactor. A large hot spot is generated frequently, thereby causing excessive oxidation in a local site in the reactor. As a result, undesirable oxidation increases, resulting in a drop in yield of the target product. Moreover, catalysts are locally exposed to high temperature conditions caused by the presence of a hot spot, resulting in degradation in lifetime of the catalysts.

A hot spot refers to a site where the highest temperature peak is generated, and is formed by the generation of reaction heat caused by catalytic vapor phase oxidation. The hot spot is determined by the composition of reactants, the flow rate (L/min) of the reactants, the temperature of a heat transfer medium, etc., and has a certain position and magnitude under a certain process condition. Generally, each catalytic layer has at least one hot spot. However, since the activity of a catalyst varies with time, the position and temperature of a hot spot may also be varied.

According to the present invention, a partition is disposed in such a manner that each shell space divided by the partition has at least one temperature peak, after the characterization of the temperature profile of a catalyst layer. By doing so, a hot spot and zones near the hot spot having the possibility of heat accumulation can be heat-controlled intensively in an independent heat-control space. As used herein, the term "each divided shell space" indicates an internal space surrounded by a catalytic tube, a shell, a partition, a tube sheet, etc.

In each reaction zone, the portions where heat control is problematic due to the hot spot include the front portion of a catalyst layer, in which main reactants including olefins, alkanes or unsaturated aldehydes, and molecular oxygen, are present at high concentrations. Also, if two or more catalyst layers are used in each step, such problematic portions include the vicinity of the boundary between the adjacent catalyst layers having different activities.

The partition is preferably located at either a position where heat control is problematic due to the hot spot or heat accumulation caused by the hot spot, or a position allowing the largest possible removal of heat generation in each zone.

Additionally, when each reaction zone is divided into two or more shell spaces by using at least one partition and is subjected to heat control, it is possible to provide the process with high flexibility under the variations in temperature profile characteristics.

(2) Heat Control of Heat Transfer Medium of the First Shell Space of Each Step

According to an aspect of the present invention, at least one of the first-step reaction zone and the second-step reaction zone is divided into two or more shell spaces by at least one partition; each of the divided shell spaces is independently heat-controlled; a heat transfer medium in the first shell space of the first-step reaction zone or the first shell space of the second-step reaction zone has a temperature ranging from the lowest active temperature of a catalyst layer packed in a reaction tube corresponding to the first shell space of the first-step reaction zone or the first shell space of the second-step reaction zone to [the lowest active temperature+20° C.], when referring to the two or more shell spaces corresponding to the first-step reaction zone sequentially as the first shell space of the first-step reaction zone, the second shell space of the first-step reaction zone, . . . , the $n^{th}$ shell space of the first-step reaction zone, and the two or more shell spaces corresponding to the second-step reaction zone sequentially as the first shell space of the second-step reaction zone, the second shell space of the second-step reaction zone, . . . , the $n^{th}$ shell space of the second-step reaction zone (wherein n is an integer of 2 or more); and the first shell space of the first-step reaction zone or the first shell space of the second-step reaction zone is controlled in such a manner that it provides a reactant conversion contribution per length as defined in Equation 1 or 2 of 1.2~2.5.

According to another aspect of the present invention, in the case of a single-step process for producing unsaturated acids from alkanes, a reaction zone for producing the unsaturated acids is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to [the lowest active temperature+20° C.], when referring to the two or more shell spaces sequentially as the first shell space, the second shell space, . . . , the $n^{th}$ shell space; and the first shell space is controlled in such a manner that it provides an alkane conversion contribution per length as defined in Equation 2 of 1.2~2.5.

As used herein, the term "the lowest active temperature of the first-step catalyst layer" refers to the lowest temperature where the olefin conversion (defined by the following Equation 3) in the relevant catalyst layer reaches 90%, when the olefins, such as propylene or the like, are allowed to react with the relevant catalyst layer at a space velocity of about 95~115 $hr^{-1}$.

The above space velocity of the olefins ranging from about 95 $hr^{-1}$ to 115 $hr^{-1}$ corresponds to a space velocity of total reaction feed gas introduced to the first-step reaction zone of about 1300~1500 $hr^-$, the feed gas comprising 7~7.5% of olefins, 13~15% of oxygen, 7~10% of water steam and the balance amount of inert gas.

[Equation 3]

Olefin conversion (%)=[mole number of reacted olefins/mole number of supplied olefins]×100

As used herein, the term "the lowest active temperature of the second-step catalyst layer" refers to the lowest temperature where the unsaturated aldehyde conversion (defined by the following Equation 4) in the relevant catalyst layer reaches 90%, when the unsaturated aldehydes are allowed to react with the relevant catalyst layer at a space velocity of about 75~100 $hr^{-1}$.

The above space velocity of the unsaturated aldehydes ranging from about 75 $hr^{-1}$ to 100 $hr^{-1}$ corresponds to a space velocity of total reaction feed gas introduced to the second-step reaction zone of about 1050~1700 $hr^{-1}$, the feed gas comprising 5~6% of unsaturated aldehydes, 5.5~6.5% of oxygen, 1~2% of unsaturated acid, 12~17% of water steam, 1~2% of byproducts and the balance amount of inert gas.

[Equation 4]

Unsaturated aldehyde conversion (%)=[mole number of reacted unsaturated aldehydes/mole number of supplied unsaturated aldehydes]×100

Meanwhile, the lowest active temperature of the catalyst layer for producing unsaturated acids from alkanes refers to the lowest temperature where the alkane conversion (defined by the following Equation 5) in the relevant catalyst layer reaches 60%, when the alkanes are allowed to react with the relevant catalyst layer at a space velocity of about 50~80 $hr^{-1}$.

The above space velocity of the alkanes ranging from about 50 $hr^{-1}$ to 80 $hr^{-1}$ corresponds to a space velocity of total reaction feed gas introduced to the reaction zone of about 1500~2000 $hr^{-1}$, the feed gas comprising 3~5% of alkanes, 10~15% of oxygen, 30~50% of water steam and the balance amount of inert gas.

[Equation 5]

Alkane conversion (%)=[mole number of reacted alkanes/mole number of supplied alkanes]×100

The lowest active temperature of a catalyst layer depends on the kind of the catalyst, content of the catalytic substance in the catalyst layer, ratio of main metal elements in the catalyst, presence of any alkali metal, kind of the alkali metal, mixing ratio with inactive materials, size of the catalyst, shape of the catalyst, sintering temperature of the catalyst, sintering atmosphere of the catalyst, and combinations thereof.

Generally, the first-step catalyst layer has an active temperature of 280~450° C., while the second-step catalyst layer has an active temperature of 250~370° C. Meanwhile, the catalyst layer for producing unsaturated acids from alkanes has an active temperature of 350~420° C.

The catalyst used in the first-step reaction zone is sintered generally at a temperature of 400~600° C., the catalyst used in the second-step reaction zone is sintered generally at a temperature of 300~500° C., and the catalyst used in the reaction zone for producing unsaturated acids from alkanes is sintered generally at a temperature of 500~600° C. If the highest peak temperature of a catalyst layer exceeds the sintering temperature where the catalyst is sintered during the preparation thereof, the catalyst layer is deteriorated, resulting in a drop in yield of the target product.

Additionally, when a catalyst layer is heated due to high reaction heat so that the hot spot temperature of the catalyst layer rapidly increases or heat accumulation occurs in the vicinity of the hot spot, oxidation forming byproducts such as COx and acetic acid occurs predominantly at such high temperature, resulting in a drop in yield of unsaturated acids.

In general, in the first-step reaction zone and/or the second-step reaction zone, and the reaction zone for producing unsaturated acids from alkanes via a single-step process, each front portion, for example, the catalyst layer corresponding to the first shell space of each step shows a high concentration of reactants (olefins, unsaturated aldehydes or alkanes) and a high reaction pressure, and consequently leads to a severe reaction. As a result, a hot spot with a significantly large magnitude is formed in the front portion of each reaction zone. Therefore, it is preferable that the reaction in the above portion is controlled in such a manner that the peak temperature of the relevant catalyst layer is significantly lower than the sintering temperature of the catalyst. Additionally, although each catalyst layer corresponding to the first shell space of each step comprises 20~30% of the total length of the catalyst layer, conversion of reactants in the first shell space reaches 50% or more. In other words, the first shell space has an excessively high load of reaction in view of its proportion to the total catalyst layer, and thus may be thermally unstabilized with ease due to the high reaction heat.

Therefore, in order to solve the aforementioned problem caused by the first shell space of each step, the temperature of the heat transfer medium in the first shell space of each step is decreased possibly to the lowest active temperature of the catalyst, according to the present invention. By doing so, it is possible to control the magnitude of a hot spot and to prevent heat accumulation in the vicinity of the hot spot, while not degrading reactivity severely.

Since a hot spot has a magnitude and a position variable depending on the kind and activity of the catalyst used in the relevant catalyst layer, the temperature of a heat transfer medium is preferably controlled considering the characteristics and reactivity of the catalyst.

The reactivity of the catalyst layer corresponding to each shell space can be expressed by the reactant conversion contribution per length, represented by Equations 1 and 2.

To satisfy the condition of the reactant conversion contribution per length being 1.2~2.5, temperature of a heat transfer medium, shear pressure (pressure of the reactor inlet), space velocity, activity of a catalyst, etc. may be controlled.

The partition dividing the first shell space of each step from the second shell space of each step is disposed in such a manner that the first shell space includes a temperature peak occurring in the inlet portion of each reaction zone.

Preferably, the first partition dividing the first shell space from the second shell space is disposed in a position corresponding to 25%~50% of the axial length of the reaction zone of each step. This indicates that contact time in the first shell space of each step corresponds to about 25%~50% of the total contact time of each step. For example, when the first-step reaction zone has a total axial length of 3000 mm, the first partition may be disposed at a point of 1200 mm, which corresponds to 40% of the total length. However, the first partition should be in such a position with the proviso that the reactant conversion contribution (defined by Equation 3, 4 or 5) of the first shell space ranges from 1.2 to 2.5.

(3) Heat Control of Heat Transfer Medium of Each Shell Space

In the production process and heat exchanger-type reactor according to the present invention, the temperature of the heat transfer medium in each shell space is set as nearly as possible to isothermal conditions. According to the amount of heat generation and the capacity of the heat transfer medium, the temperature difference between portions of the heat transfer medium, which correspond to both the ends of a catalyst layer in each of the divided shell spaces, is preferably 0-5° C., and more preferably 0-3° C.

Examples of the heat transfer medium include a very highly viscous medium, for example a molten salt which consists mainly of a mixture of potassium nitrate and sodium nitrite. Other examples of the heat transfer medium include a phenyl ether medium (e.g., "Dowtherm"), polyphenyl media (e.g., "Therm S"), hot oil, a naphthalene derivative (S.K. oil) and mercury.

By controlling the flow rate of the heat transfer medium, the reaction throughout the tube corresponding to each of the shell spaces in the reactor can be carried out at substantially the same molten salt temperature.

When heat transfer media filled in shell spaces have different temperatures along the flow direction (also referred to as the axial direction hereinafter) of reactants, reactivity of the relevant catalyst layer varies in proportion to the temperature.

It is preferable to set the temperature of the heat transfer medium (molten salt or heat transfer salt) in each of the divided shell spaces in such a manner that the relevant catalyst layer has optimal activity.

Particularly, the temperature of the heat transfer media can be varied in the axial direction according to the present invention. Thus, it is possible to inhibit the catalyst from being damaged by an excessively high exothermic reaction and to prevent degradation in yield of the target product, resulting in improvement of the yield.

The temperature of the heat transfer media in the adjacent shell spaces in each of the reaction zones is preferably set to cause a temperature difference 0-50° C., and more preferably 5-15° C. along the axial direction.

In the case of the first-step reaction zone, it is preferred that the temperature of the heat transfer medium in each of the first shell space of the first step, the second shell space of the first step, . . . , the $n^{th}$ shell space of the first step, divided by partitions, is set in such a manner that the temperature of each heat transfer medium increases along the axial direction.

In the case of the second-step reaction zone, the heat transfer medium in each of the first shell space of the second step, the second shell space of the second step, . . . , the $n^{th}$ shell space of the second step, divided by partitions, does not increase or decrease monotonously, because the product of the first step is supplied to the reaction zone corresponding to the first shell space of the second step. It is preferred to set the temperature of the heat transfer medium in each shell space in such a manner that the temperature of the heat transfer medium increases monotonously from the second shell space to the $n^{th}$ shell space except the first shell space, and the temperature of the first shell space is set according to the manner as described hereinafter related to the temperature setting in the second-step reaction zone.

Meanwhile, in the case of the reaction zone for producing unsaturated acids from alkanes via a single-step process, it is preferred that the temperature of the heat transfer medium circulating in each of the first shell space, the second shell space, ..., the $n^{th}$ shell space, divided by partitions, is set in such a manner that the temperature of each heat transfer medium increases along the axial direction.

Further, according to the present invention it is preferred that $T_{h1}-T_{salt1} \leq 150°$ C., more preferably $T_{h1}-T_{salt1} \leq 110°$ C., and $T_{hN}-T_{saltN} \leq 120°$ C., more preferably $T_{hN}-T_{saltN} \leq 100°$ C. (wherein N is an integer of 2 or more), when referring to the shell spaces divided by partitions in the first-step reaction zone for producing unsaturated aldehydes from olefins or the reaction zone for producing unsaturated acids from alkanes sequentially as the first shell space, the second shell space, ..., the $n^{th}$ shell space.

In addition, it is preferred that $T_{h1}-T_{salt1} \leq 130°$ C., more preferably $T_{h1}-T_{salt1} \leq 75°$ C., and $T_{hN}-T_{saltN} \leq 110°$ C., more preferably $T_{hN}-T_{saltN} \leq 70°$ C. (wherein N is an integer of 2 or more), when referring to the shell spaces divided by partitions in the second-step reaction zone for producing unsaturated acids from unsaturated aldehydes sequentially as the first shell space, the second shell space, ..., the $n^{th}$ shell space.

Herein, $T_{h1}$ is the highest peak temperature of a reaction mixture in the catalyst layer corresponding to the first shell space (the highest peak temperature of the catalyst layer), and $T_{hN}$ is the highest peak temperature of the reaction mixture in the catalyst layer corresponding to the $n^{th}$ shell space (the highest peak temperature of the catalyst layer). Additionally, $T_{salt1}$ is the temperature of the heat transfer medium filled in the first shell space, and $T_{saltN}$ is the temperature of the heat transfer medium filled in the $n^{th}$ shell space.

In the first shell space, the concentration and pressure of reactants are high, so that the temperature difference between the highest peak temperature of the catalyst layer and the temperature of the heat transfer medium is higher than that in the next shell space. For this reason, the temperature difference range in the first shell space will be surely wider than those in the next shell spaces. However, the present invention provides a method by which the magnitude of peak temperature in the first shell space is minimized while a temperature difference in the next shell space is limited in an extended range, thereby forming an overall temperature profile having a smooth shape.

According to the present invention, the temperature difference between the highest peak temperature of a catalyst layer in each reaction zone and the temperature of a heat transfer medium is controlled as described above, so that the catalyst can show uniform activity in the axial direction. Thus, it is possible to inhibit heat accumulation in a hot spot and suppress side reactions, thereby preventing a drop in yield.

(4) Constitution of Catalyst Layers

The catalyst layer in the first-step reaction zone may consist of one layer with axially uniform activity, or if necessary, two or more stacked layers with increasing activity. The catalyst layer in the second-step reaction zone may consist of one layer with axially uniform activity, or if necessary, two or more stacked layers with increasing activity. The catalyst layer of the reaction zone for producing unsaturated acids from alkanes may be formed in the same manner as described above.

(5) Constitution of Reaction Inhibition Layer

Preferably, a layer formed of an inactive material or a mixture of an inactive material and a catalytic material, i.e., a reaction inhibition layer, is disposed within a portion of the catalytic tube, which corresponds to a position where the partition is disposed. By doing so, it is possible to eliminate a problem in heat transfer at the position where the partition is disposed.

A commercially available shell-and-tube reactor for producing (meth)acrylic acid includes catalytic tubes in the number of several hundreds to several tens of thousands, and a partition disposed in such a reactor has a relatively large thickness of 50~100 mm. Therefore, in the reaction zone of each step having two or more divided shell spaces, it is difficult to remove the reaction heat at the portion where a partition is disposed, thereby causing a problem in heat transfer. To solve this problem, it is preferred to dispose a layer formed of an inactive material or a mixture of an inactive material and a catalytic material, i.e., a reaction inhibition layer within a portion of the catalytic tube, which corresponds to a position where the partition is disposed.

In the reaction inhibition layer, the volume ratio of an inactive material to a catalytic material in this reaction inhibition layer is 20~100%.

The inactive material used in the reaction inhibition layer is designated as a material which is inactive to a reaction for producing unsaturated aldehydes and/or unsaturated acids from olefins and/or alkanes, for example, catalytic oxidation of propylene or the like and (meth)acrolein. It can be used in a sphere, cylinder, ring, rod, plate or wire mesh shape, or a mass shape with suitable size, or a suitable combination thereof. Widely known examples of the inactive material include alumina, silica alumina, stainless steel, iron, steatite, porcelain, various ceramics, and mixtures thereof.

Preferably, the reaction inhibition layer is packed to a height corresponding to 20~500% of the thickness of a partition.

The heat control system according to the present invention can be applied not only to oxidation of olefins but also to a reaction system for carrying out different reactions along the axial direction in a stepwise manner and a reaction system requiring independent heat control of every reaction zone to the optimal temperature even if the reaction zones perform the same reaction.

BEST MODE FOR CARRYING OUT THE INVENTION

Figure 1:
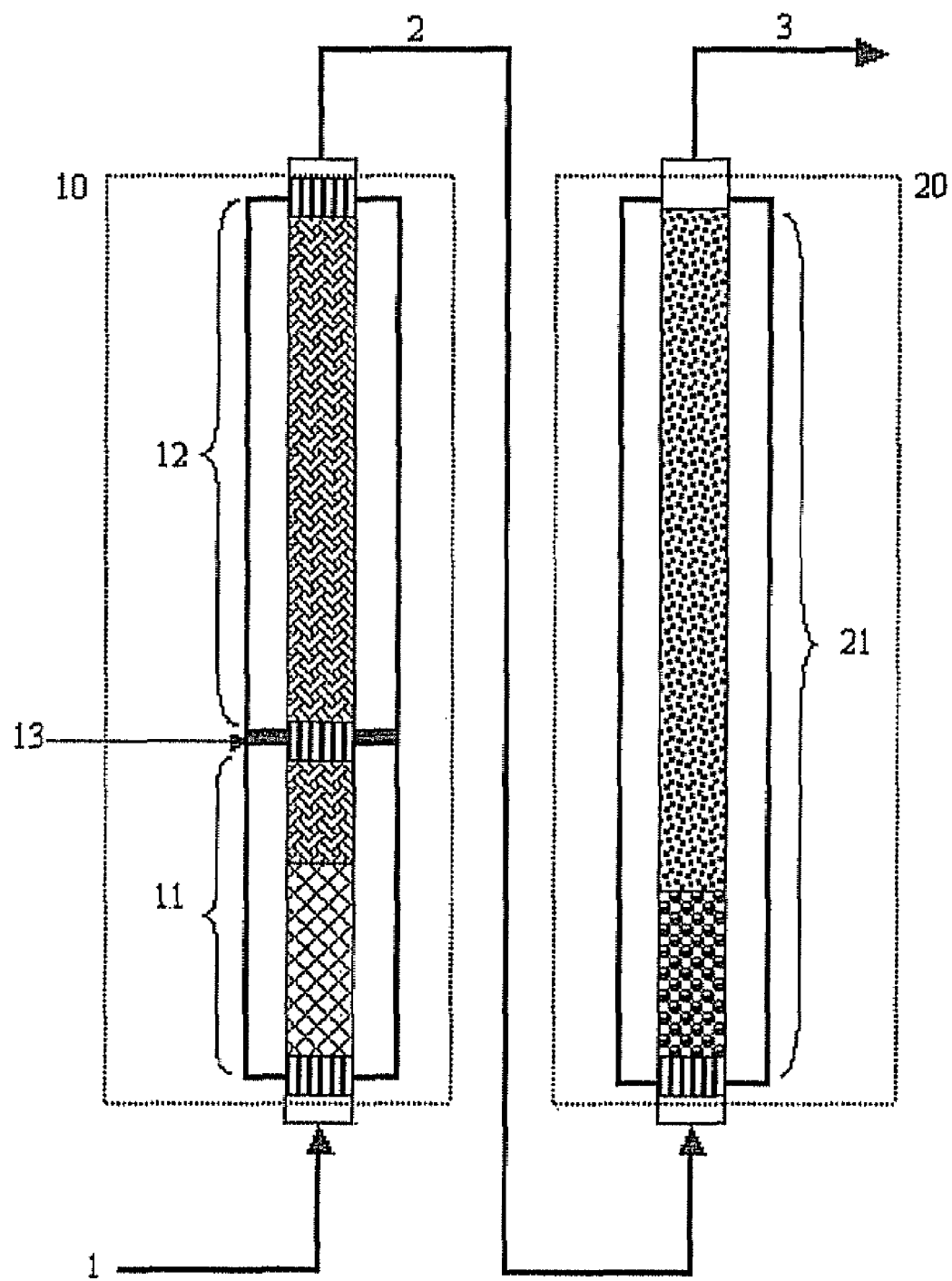
FIG. 1 is a schematic diagram showing the structure of a reactor according to Example 1, which illustrates the position of a partition and a catalyst layer disposed inside a catalytic tube.

Reference will now be made in detail to the preferred embodiments of the present invention. It is to be understood that the following examples are illustrative only and the present invention is not limited thereto.

REFERENCE EXAMPLE 1

Determination of Lowest Active Temperature of Catalyst Layer Corresponding to First Shell Space of First Step A pilot reactor in which the first step is conducted in one catalytic tube was provided. The catalytic tube had an inner diameter of 26 mm. In the first-step catalytic tube, a catalyst layer was packed to a height of about 1200 mm. At this time, two kinds of catalysts having activity increasing along the axial direction from the inlet to the outlet were packed to a height of 320 mm and 880 mm, respectively (see "Method of Controlling Catalytic Activity" described in U.S. Pat. Nos. 3,801,634 and 4,837,360). The catalyst was comprised of the first-step oxidation catalyst material obtained according to the method as disclosed in Korean Patent Publication No. 0349602 (Korean Patent Application No. 10-1997-0045132), the catalyst material being based on molybdenum (Mo) and bismuth (Bi).

The first catalyst layer (referred to as LGC1 hereinafter) of the first-step reaction zone showed an activity corresponding to 85~90% of the catalytic activity of the second catalyst layer, when measuring the catalytic activity by propylene conversion (space velocity of propylene 98 hr–1, molten salt temperature of 300° C.)

Like the following Example 1, the first shell space included the peak portion of the second catalyst layer, and the catalyst layer of the first shell space had a length of 540 mm.

The starting materials introduced into the inlet of the reactor were comprised of propylene, oxygen, steam and nitrogen gas, wherein propylene content was 7% and the ratio of oxygen to propylene was about 1.80. Based on the catalyst layer corresponding to the first shell space of the first-step reaction zone (catalyst layer of 540 mm corresponding to the first shell space), space velocity was 1400 $hr^{-1}$ (standard temperature and pressure, STP), and space velocity of the olefins introduced into the first-step reaction zone was 98 $hr^{-1}$ (STP).

Space velocity=flow rate of feed (L/hr, STP)/volume of catalyst layer (L)

The above conditions were the same as those of the following Example 1, with the exception of the space velocity and the temperature of molten salt.

(1) When the molten salt filled in the first shell space of the first step was set to a temperature of 285° C., it was shown that propylene conversion was 86.2% after the analysis of the gas obtained from the outlet of the first shell space of the first step.

(2) When the molten salt filled in the first shell space of the first step was set to a temperature of 290° C., it was shown that propylene conversion was 88.3% after the analysis of the gas obtained from the outlet of the first shell space of the first step.

(3) When the molten salt filled in the first shell space of the first step was set to a temperature of 295° C., it was shown that propylene conversion was 90.8% after the analysis of the gas obtained from the outlet of the first shell space of the first step.

(4) As can be seen from the above results, the catalyst layer used in Reference Example 1 has the lowest active temperature of 290° C.

Example 1

Variations in Yield and in Magnitudes of Temperature Peaks at Hot Spots Depending on Variations in Temperature Setting of Molten Salt As shown in FIG. 1, a pilot reactor was provided in which each of first-step reaction and second-step reaction is conducted in one catalytic tube (included in zone 10 or 20 of FIG. 3). The catalytic tube had an inner diameter of 26 mm, and the first-step catalytic tube was filled with catalyst layers to a height of about 1200 mm, and the second-step catalytic tube was filled with catalyst layers to a height of about 1100 mm.

In the catalyst layers of the first step reaction zone 10, two kinds of catalysts having activity increasing along the axial direction from the inlet to the outlet were packed to a height of 320 mm and 880 mm, respectively (see "Method of Controlling Catalytic Activity" described in U.S. Pat. Nos. 3,801,634 and 4,837,360) . In the catalyst layers of the second-step reaction zone 20, two kinds of catalysts having activity increasing along the axial direction from the inlet to the outlet were packed a height of 290 mm and 810 mm, respectively.

The catalyst layers of the first-step reaction zone were comprised of the first-step oxidation catalyst material obtained according to the method as disclosed in Korean Patent Publication No. 0349602 (Korean Patent Application No. 10-1997-0045132), the catalyst material being based on molybdenum (Mo) and bismuth (Bi). The catalyst layers of the second-step reaction zone were comprised of a catalyst based on molybdenum and vanadium (V), the preparation of which is described in Korean patent No. 0204728 or Korean patent No. 0204729.

In the first catalyst layer of the first-step reaction zone, LGC1 catalyst was used. The catalyst showed an activity corresponding to 85~90% of the catalytic activity of the second catalyst layer, when measuring the catalytic activity by propylene conversion (space velocity of propylene 98 hr–1, molten salt temperature of 300° C.).

The first catalyst layer of the second-step reaction zone showed an activity corresponding to 85~90% of the catalytic activity of the second catalyst layer.

A partition was disposed at the 600-mm position (central portion) of the first-step reaction zone, so that the first shell space of the first step covered both temperature peaks occurring in the first catalyst layer of the first step and the second catalyst layer of the first step. In a portion inside the catalytic tube corresponding to the position of the partition, an inactive material layer was filled to a thickness corresponding 120% of the thickness of the partition.

Reference numerals 11 and 12 in FIG. 1 illustrate the shell spaces divided in the first-step reaction zone. Each molten salt filled in each shell space was set to a temperature of 308° C. and 315° C., respectively. Reference numeral 21 in FIG. 1 illustrate a shell space of the second-step reaction zone, the shell space being filled with a molten salt set to a temperature of 265° C.

A pipe inducing a flow represented by reference numeral 2 in FIG. 1 serves to connect the two catalytic tubes and is surrounded by a heat insulation material. Starting materials comprising propylene, steam, oxygen and inert gas enter the reactor through a line 1, passes through the reaction steps, and then flows out from the reactor through a line 3. The starting materials were comprised of propylene, oxygen, steam and nitrogen gas, wherein the propylene content was 7% and the ratio of oxygen to propylene was about 1.80. Space velocity was 1400 $hr^{-1}$ (standard temperature and pressure, STP) in the total first-step reaction zone, and 1530 $hr^{-1}$ (STP) in the total second-step reaction zone. Also, the space velocity of olefins introduced into the first-step reaction zone was 98 $hr^{-1}$ (STP).

In the first shell space of the first step, the value defined by Equation 1 was about 2.

A hot spot was generated in the zone corresponding to the first shell space of the first-step reaction zone, the hot spot having a temperature of 392.5° C. After the reaction in the first-step reaction zone, acrolein and acrylic acid were obtained in a yield of 80.33% and 11.37%, respectively. In the second-step reaction zone operated under isothermal conditions, a hot spot having a temperature of 320.5° C. was generated. After the reaction in the second-step reaction zone, acrolein and acrylic acid were obtained in a yield of 0.631% and 86.83%, respectively.

Since no reaction occurred in the reaction inhibition layer (inactive material layer), no abnormal increase in temperature caused by a drop in heat transfer efficiency could be observed.

Example 2

Variations in Yield and in Magnitudes of Temperature Peaks at Hot Spots Depending on Variations in Temperature Setting of Molten Salt This example was performed in the same manner as described in Example 1, except that the temperatures of the molten salt in the first-step reaction zone (first-step reactor) were set to 300° C. and 315° C., respectively, in an axial direction. In the first shell space of the first step, the value defined by Equation 1 was about 1.9.

In the zone corresponding to the first shell space in the first-step reaction zone, a hot spot with a temperature of 381.2° C. was generated. The yields of acrolein and acrylic acid were 79.02% and 11.46%, respectively. In the second-step reaction zone operated under isothermal conditions, the temperature of a hot spot was 327.5° C., and the yields of acrolein and acrylic acid were 0.607% and 84.95%, respectively.

Comparative Example 1

This example was performed in the same manner as described in Example 1, except that the temperature of the molten salt filled in each shell space of the first-step reaction zone was set to 310° C. The temperature, 310° C., of the molten salt in the first-step reaction zone is higher than the lowest active temperature by 20° C.

Comparative Example 2

This example was performed in the same manner as described in Example 1, except that the temperature of the molten salt filled in each shell space of the first-step reaction zone was set to 320° C. The temperature, 320° C., of the molten salt in the first-step reaction zone is higher than the lowest active temperature by 30° C.

As the highest peak temperature of the first-step catalyst layer exceeds 430° C., the catalyst layer was damaged so that the total propylene conversion decreased rapidly to a level less than 90%. So, the test was terminated.

Before the catalyst layer was damaged, conversion in the portion corresponding to the first shell space of the first step according to Comparative Example 2 was analyzed. As a result, the value defined by Equation 1 was 3.01.

Comparative Example 3

This example was performed in the same manner as described in Example 1, except that the temperature of the molten salt filled in each shell space of the first-step reaction zone was set to 312° C. The temperature, 312° C., of the molten salt in the first-step reaction zone is higher than the lowest active temperature by 22° C.

In the first-step reactor operated under isothermal conditions, a hot spot with a temperature of 409.1° C. was generated. The yields of acrolein and acrylic acid were 78.8% and 11.9%, respectively. In the second-step reaction zone operated under isothermal conditions, the temperature of a hot spot was 329.2° C., and the yields of acrolein and acrylic acid were 0.367% and 85.08%, respectively.

After the analysis of the conversion in the portion corresponding to the first shell space of the first step according to Comparative Example 3, the value defined by Equation 1 was 2.63.

TABLE 1

| Reaction zone | | Ex. 1 | Ex. 2 | Comp. Ex. 1 | Comp. Ex. 2 | Comp. Ex. 3 |
| --- | --- | --- | --- | --- | --- | --- |
| First step | Temperature of molten salt (° C.) | 308 315 | 300 315 | 310 310 | 320 320 | 312 312 |
| | Temperature of hot spot (° C.) | 392.5 | 381.2 | 405.7 | >430 | 409.1 |
| | Acrolein | 80.33% | 79.01% | 80.43% | — | 78.8% |
| | Acrylic acid | 11.37% | 11.46% | 10.11% | — | 11.9% |
| Second step | Temperature of molten salt (° C.) | 265 | 265 | 265 | 265 | 265 |
| | Temperature of hot spot (° C.) | 320.5 | 327.5 | 316.0 | — | 329.2 |
| | Acrolein | 0.631% | 0.607% | 1.257% | — | 0.367% |
| | Acrylic acid | 86.83% | 84.95% | 84.66% | — | 85.08% |

In the first-step reactor operated under isothermal conditions, a hot spot with a temperature of 405.7° C. was generated. The yields of acrolein and acrylic acid were 80.43% and 10.11%, respectively. In the second-step reaction zone operated under isothermal conditions, the temperature of a hot spot was 316.0° C., and the yields of acrolein and acrylic acid were 1.257% and 84.66%, respectively.

After the analysis of the conversion in the portion corresponding to the first shell space of the first step according to Comparative Example 1, the value defined by Equation 1 was 2.7.

REFERENCE EXAMPLE 2

Figure 2:
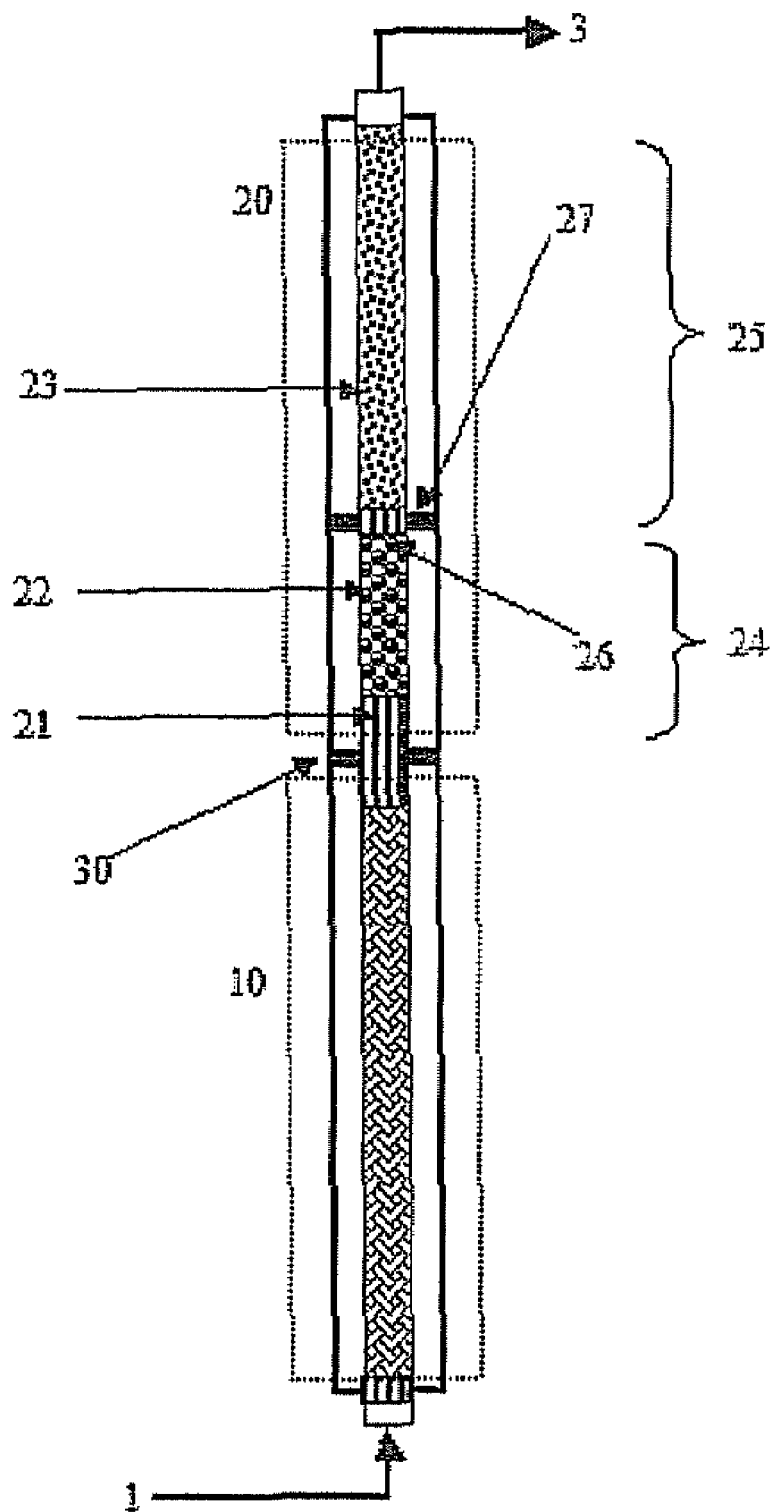
FIG. 2 is a schematic diagram showing the structure of a reactor according to Example 3, which illustrates the position of a partition and a catalyst layer disposed inside a catalytic tube.

Determination of Lowest Active Temperature of Catalyst Layer Corresponding to First Shell Space of Second Step A pilot reactor in which the first-step reaction and the second-step reaction are conducted in one catalytic tube was provided. The catalytic tube had an inner diameter of 26 mm. In the catalytic tube, a first-step catalyst layer was packed to a height of about 3570 mm, and the second-step catalyst layer was packed to a height of about 3125 mm. Herein, the catalyst material filled in the first-step reaction zone (reference numeral 10 in FIG. 2) was the first-step oxidation catalyst material obtained according to the method as disclosed in Korean Patent Publication No. 0349602 (Korean Patent Application No. 10-1997-0045132), the catalyst material being based on molybdenum (Mo) and bismuth (Bi). The three catalyst layers filled in the second-step reaction zone (reference numeral 20 in FIG. 2) were comprised of a catalyst based on molybdenum and vanadium (V), the preparation of which is described in Korean patent No. 0204728 or Korean patent No. 0204729.

The second-step catalyst layers were comprised of three kinds of catalysts having activity increasing along the axial direction from the inlet to the outlet (see "Method of Controlling Catalytic Activity" described in U.S. Pat. Nos. 3,801,634 and 4,837,360). The first catalyst layer (reference numeral 21 in FIG. 2) of the second-step reaction zone, from which the second-step reaction started, showed an activity corresponding to about 20% of the catalytic activity of the third catalyst layer of the second step (reference numeral 23 in FIG. 2). This was accomplished by forming the first catalyst layer with a mixture containing 20 wt % of the same catalyst material as the third catalyst layer and 80 wt % of an inactive material. The second catalyst layer of the second step (reference numeral 22 in FIG. 2) showed an activity corresponding to 87% of the catalytic activity of the third catalyst layer of the second step.

The three catalyst layers of the second-step reaction zone were packed to a height of 500 mm, 700 mm and 1925 mm, respectively, along the axial direction. The first catalyst layer of the second step was packed to a height of 250 mm in the catalytic tube corresponding to the shell spaces of the second-step reaction zone, and the remaining 250 mm was disposed in the partition (reference numeral 30 in FIG. 2), by which the first-step reaction zone was divided from the second-step reaction zone, and in the catalytic tube covering the shell spaces of the first-step reaction zone.

The second-step reaction zone was divided into two independent shell spaces (reference numerals 24 and 25 in FIG. 2) by the partition (reference numeral 27 in FIG. 2) disposed in the boundary between the second catalyst layer of the second step and the third catalyst layer of the second step. Meanwhile, an inactive material layer was packed in the catalytic tube at the portion corresponding to the position of the partition to a height corresponding to 120% of the thickness of the partition.

The starting materials introduced into the inlet of the second-step reaction zone (i.e., the partition 30 by which the first-step reaction zone was divided from the second-step reaction zone) were comprised of acrolein, acrylic acid, oxygen, steam and nitrogen gas, more particularly, 5.5% of acrolein, 0.9% of acrylic acid, 5.0% of oxygen, 1.0% of byproducts such as COx and acetic acid, and the balance amount of nitrogen gas.

In the catalyst layers corresponding to the first shell space of the second-step reaction zone (catalyst layer of 950 mm corresponding to 250 mm of the first catalyst layer combined with 700 mm of the second catalyst layer), space velocity was 1500 hr$^{-1}$ (standard temperature and pressure, STP). Herein, space velocity of the hydrocarbon reactant, i.e. acrolein, introduced into the second-step reaction zone was 81 hr$^{-1}$ (STP) and the feed gas mixture had a pressure of 0.4 kgf/cm$^2$G.

The above conditions were the same as those of the following Example 3, with the exception of the space velocity and the temperature of molten salt.

(1) When the molten salt filled in the first shell space of the second step was set to a temperature of 255° C., it was shown that the conversion defined by Equation 4 was 83.1% after the analysis of the gas obtained from the outlet of the first shell space of the second step.

(2) When the molten salt filled in the first shell space of the second step was set to a temperature of 260° C., it was shown that the conversion defined by Equation 4 was 91.9% after the analysis of the gas obtained from the outlet of the first shell space of the second step.

As can be seen from the above results, the catalyst layer has the lowest active temperature of 260° C.

Example 3

Use of Mixed Layers and Multi-step Heat Control System

A pilot reactor in which the first-step reaction and the second-step reaction are conducted in one catalytic tube was provided. The catalytic tube had an inner diameter of 26 mm. In the catalytic tube, a first-step catalyst layer was packed to a height of about 3570 mm, and the second-step catalyst layer was packed to a height of about 3125 mm. Herein, the catalyst material filled in the first-step reaction zone (reference numeral 10 in FIG. 2) was the first-step oxidation catalyst material obtained according to the method as disclosed in Korean Patent Publication No. 0349602 (Korean Patent Application No. 10-1997-0045132), the catalyst material being based on molybdenum (Mo) and bismuth (Bi). The three catalyst layers filled in the second-step reaction zone (reference numeral 20 in FIG. 2) were comprised of a catalyst based on molybdenum and vanadium (V), the preparation of which is described in Korean patent No. 0204728 or Korean patent No. 0204729.

The second-step catalyst layers were comprised of three kinds of catalysts having activity increasing along the axial direction from the inlet to the outlet (see "Method of Controlling Catalytic Activity" described in U.S. Pat. Nos. 3,801,634 and 4,837,360). The first catalyst layer (reference numeral 21 in FIG. 2) of the second-step reaction zone, from which the second-step reaction started, showed an activity corresponding to about 20% of the catalytic activity of the third catalyst layer of the second step (reference numeral 23 in FIG. 2). This was accomplished by forming the first catalyst layer with a mixture containing 20 wt % of the same catalyst material as the third catalyst layer and 80 wt % of an inactive material. The second catalyst layer of the second step (reference numeral 22 in FIG. 2) showed an activity corresponding to 87% of the catalytic activity of the third catalyst layer of the second step.

The three catalyst layers of the second-step reaction zone were packed to a height of 500 mm, 700 mm and 1925 mm, respectively, along the axial direction. The first catalyst layer of the second step was packed to a height of 250 mm in the catalytic tube corresponding to the shell spaces of the second-step reaction zone, and the remaining 250 mm was disposed in the partition (reference numeral 30 in FIG. 2), by which the first-step reaction zone was divided from the second-step reaction zone, and in the catalytic tube covering the shell spaces of the first-step reaction zone.

The second-step reaction zone was divided into two independent shell spaces (reference numerals 24 and 25 in FIG. 2) by the partition (reference numeral 27 in FIG. 2) disposed in the boundary between the second catalyst layer of the second step and the third catalyst layer of the second step. Each molten salt filled in each shell space was set to a temperature of 275° C. and 270° C., respectively. Meanwhile, an inactive material layer was packed in the catalytic tube at the portion corresponding to the position of the partition to a height corresponding to 120% of the thickness of the partition (reference numeral 26 in FIG. 2).

The starting materials introduced into the inlet of the second-step reaction zone, (i.e. the partition 30, by which the first-step reaction zone was divided from the second-step reaction zone) were comprised of acrolein, acrylic acid, oxygen, steam and nitrogen gas, more particularly, 5.5% of acrolein, 0.9% of acrylic acid, 5.0% of oxygen, 1.0% of byproducts such as COx and acetic acid, and the balance amount of nitrogen gas. In the total second-step reaction zone, space velocity was 1500 $hr^{-1}$ (standard temperature and pressure, STP). Herein, space velocity of the hydrocarbon reactant, i.e. acrolein, introduced into the second-step reaction zone was 81 $hr^{-1}$ (STP) and the feed gas mixture had a pressure of 0.4 $kgf/cm^2G$.

In the reaction zone corresponding to the first shell space of the second step, the value defined by Equation 2 was about 2.

In the second-step reaction zone, two catalyst layers of the three catalyst layers except the mixed layer (i.e. the first catalyst layer) had a temperature peak. The two peak temperatures were 309.4° C. and 321.7° C. along the axial direction. When the propylene content introduced into the first step was 7.0%, yield of acrylic acid was 86.2%. Yields of byproducts, COx (carbon monooxide and carbon dioxide) and acetic acids, were 8.51% and 1.80%, respectively.

The reaction mixture arriving in the first catalyst layer of the second step along the axial direction had a temperature of 316° C., and the temperature difference between the above temperature and the first heat transfer medium of the second step was 41°C.

Comparative Example 4

This example was performed in the same manner as described in Example 3, except that the temperature of the molten salt filled in each shell space of the second-step reaction zone was set to 285° C. The temperature, 285° C., is higher than the lowest active temperature by 25° C., and thus is not included in the scope of the present invention.

In the reaction zone corresponding to the first shell space of the second step according to Comparative Example 4, the value defined by Equation 2 was about 2.2, which was included in the scope of the present invention. In the second-step reaction zone, two catalyst layers of the three catalyst layers except the mixed layer (i.e. the first catalyst layer) had a temperature peak. The two peak temperatures were 331.3° C. and 328.1° C along the axial direction. Yield of acrylic acid was 83.8%, and the yields of byproducts, COx (carbon monooxide and carbon dioxide) and acetic acid were 11.3% and 2.12%, respectively.

TABLE 2

| Reaction zone | | Ex. 3 | Comp. Ex. 4 |
| --- | --- | --- | --- |
| Second step | Temperature of molten salt (° C.) | 275 270 | 285 285 |
| | Temperature of hot spot (° C.) | 309.4 321.7 | 331.3 328.1 |
| | Acrylic acid | 86.2% | 83.8% |

INDUSTRIAL APPLICABILITY

As described above, the present invention provides an improved system in which the temperature of a heat transfer medium in each shell space is controlled depending on the activity of a catalyst and the degree of reaction. By doing so, it is possible to inhibit heat accumulation in a hot spot and the vicinity thereof, and thus to ensure thermal stability, to reduce the production of byproducts and to improve the yield of a final product.

The invention claimed is:

1. A process for producing unsaturated aldehydes from olefins by fixed-bed catalytic partial oxidation in a shell-and-tube heat exchanger-type reactor, wherein the reactor comprises a reaction zone for producing the unsaturated aldehydes; the reaction zone is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to the lowest active temperature of the catalyst layer plus 20° C., wherein the two or more shell spaces are sequentially referred to as the first shell space, the second shell space, . . ., the $n^{th}$ shell space; and the first shell space is controlled in such a manner that it provides an olefin conversion contribution per length as defined in a following equation of 1.2 to 2.5:

olefin conversion contribution per length =(mole number of olefins that have reacted in the relevant catalyst layer zone / mole number of the total olefins supplied to the the reaction zone) / volumetric ratio of the revelant catalyst layer zone to the total catalyst layer of the reaction zone.

2. A process for producing unsaturated acids from unsaturated aldehydes or alkanes by fixed-bed catalytic partial oxidation in a shell-and-tube heat exchanger-type reactor, wherein the reactor comprises a reaction zone for producing the unsaturated acids; the reaction zone is divided into two or more shell spaces by at least one partition; each of the divided shell spaces is independently heat-controlled; a heat transfer medium in the first shell space has a temperature ranging from the lowest active temperature of a catalyst layer packed in a reaction tube corresponding to the first shell space to the lowest active temperature of the catalyst layer plus 20° C., wherein the two or more shell spaces are sequentially referred to as the first shell space, the second shell space, . . ., the $n^{th}$ shell space; and the first shell space is controlled in such a manner that it provides an unsaturated aldehyde or alkane conversion contribution per length as defined in a following equation of 1.2 to 2.5:

unsaturated aldehyde or alkane conversion contribution per length =(mole number of unsaturated aldehydes or alkanes that have reacted in the relevant catalyst layer zone/mole number of the total unsaturated aldehydes or alkanes supplied to the reaction zone)/volumetric ratio of the relevant catalyst layer zone to the total catalyst layer of the reaction zone.

3. The process according to claim 1, which is for producing (meth)acrolein from at least one compound selected from the group consisting of propylene, isobutylene, t-butyl alcohol, methyl-t-butyl ether and o-xylene.

4. The process according to claim 2, which is for producing (meth)acrylic acid from (meth)acrolein, propane or isobutane.

5. The process according to claim 1, wherein the partition dividing the first shell space from the second shell space is disposed in such a manner that the first shell space covers a temperature peak generated in a front portion of each reaction zone.

6. The process according to claim 5, wherein the partition dividing the first shell space from the second shell space is disposed in a position corresponding to 25% to 50% of the axial length of each reaction zone.

7. The process according to claim 2, wherein the partition dividing the first shell space from the second shell space is disposed in such a manner that the first shell space covers a temperature peak generated in a front portion of each reaction zone.

8. The process according to claim 7, wherein the partition dividing the first shell space from the second shell space is disposed in a position corresponding to 25% to 50% of the axial length of each reaction zone.

9. The process according to claim 1, the first shell space, the second shell space, . . . the $n^{th}$ shell space, divided by the partitions are controlled in such a manner that temperature of the heat transfer medium circulating in each shell space increases along the axial direction.

10. The process according to claim 2, which is for producing unsaturated acids from unsaturated aldehydes, wherein the second shell space through the $n^{th}$ shell space divided by the partitions are controlled in such a manner that temperature of the heat transfer medium circulating in each shell space increases along the axial direction.

11. The process according to claim 2, which is for producing unsaturated acids from alkanes, wherein the first shell space, the second shell space, . . ., the $n^{th}$ shell space divided by the partitions are controlled in such a manner that temperature of the heat transfer medium circulating in each shell space increases along the axial direction.

12. The process according to claim 1, wherein $T_{h1}$-$T_{salt1}$ ° C. 150 ° C., and $T_{hN}$-$T_{saltN}$ ° C. 120° C. wherein N is an integer of 2 or more; $T_{h1}$ is the highest peak temperature of a reaction mixture in a catalyst layer corresponding to the first shell space; $T_{hN}$ is the highest peak temperature of a reaction mixture in a catalyst layer corresponding to the $n^{th}$ shell space; $T_{salt1}$ is the temperature of a heat transfer medium filled in the first shell space; and $T_{saltN}$ is the temperature of a heat transfer medium filled in the $n^{th}$ shell space.

13. The process according to claim 2, which is for producing unsaturated acids from unsaturated aldehydes, wherein $Th_{h1}$-$T_{salt1}$ ° C. 130 ° C., and $Th_{hn}$-$T_{saltN}$ ° C. 110 ° C. wherein N is an integer of 2 or more; $Th_{hN}$ is the highest peak temperature of a reaction mixture in a catalyst layer corresponding to the first shell space; $T_{hN}$ is the highest peak temperature of a reaction mixture in a catalyst layer corresponding to the $n^{th}$ shell space; $T_{salt1}$ is temperature of a heat transfer medium filled in the first shell space; and $T_{saltN}$ is the temperature of a heat transfer medium filled in the $n^{th}$ shell space.

14. The process according to claim 2, which is for producing unsaturated acids from alkanes, wherein $Th_1$-$T_{salt1}$° C. 150 ° C., and $Th_{hN}$-$T_{saltN}$ ° C. 120 ° C. wherein N is an integer of 2 or more; $T_{h1}$ is the highest peak temperature of a reaction mixture in a catalyst layer corresponding to the first shell space; $Th_{hN}$ is the highest peak temperature of a reaction mixture in a catalyst layer corresponding to the $n^{th}$ shell space; $T_{salt1}$ is the temperature of a heat transfer medium filled in the first shell space; and $T_{saltN}$ is the temperature of a heat transfer medium filled in the $n^{th}$ shell space.

15. The process according to claim 1, wherein a reaction inhibition layer formed of an inactive material alone or a mixture of inactive materials and a catalyst is placed within the catalytic tube in a position corresponding to the position of the partition.

16. The process according to claim 2, wherein a reaction inhibition layer formed of an inactive material alone or a mixture of inactive materials and a catalyst is placed within the catalytic tube in a position corresponding to the position of the partition.

* * * * *